United States Patent [19]

Maurer et al.

[11] 4,283,261
[45] Aug. 11, 1981

[54] ELECTROCHEMICAL SENSOR STRUCTURE TO DETERMINE OXYGEN CONTENT IN COMBUSTION EXHAUST GASES

[75] Inventors: Helmut Maurer, Schwieberdingen; Klaus Müller, Tamm; Franz Rieger, Aalen-Wasseralfingen; Ernst Linder, Mühlacker; Hermann Dietz, Gerlingen; Karl-Hermann Friese, Leonberg; Bodo Ziegler, Stuttgart, all of Fed. Rep. of Germany

[73] Assignee: Robert Bosch GmbH, Stuttgart, Fed. Rep. of Germany

[21] Appl. No.: 100,256

[22] Filed: Dec. 4, 1979

[30] Foreign Application Priority Data

Dec. 20, 1978 [DE] Fed. Rep. of Germany ....... 2855012

[51] Int. Cl.³ .......................................... G01N 27/46
[52] U.S. Cl. .................................................. 204/195 S
[58] Field of Search .......................... 204/1 S, 195 S

[56] References Cited

U.S. PATENT DOCUMENTS

| | | | |
|---|---|---|---|
| 3,468,780 | 9/1969 | Fischer | 204/195 S |
| 3,691,023 | 9/1972 | Ruka et al. | 204/195 S |
| 3,696,007 | 10/1972 | Bennett et al. | 204/195 W |
| 3,719,564 | 3/1973 | Lilly et al. | 204/1 S |
| 3,767,469 | 10/1973 | Flais et al. | 204/195 S |
| 3,954,590 | 5/1976 | Czuha | 204/195 W |
| 3,978,006 | 8/1976 | Topp et al. | 204/195 S |
| 3,989,614 | 11/1976 | Tien | 204/197 |
| 4,005,001 | 1/1977 | Pebler | 204/195 S |
| 4,021,326 | 5/1977 | Pollner et al. | 204/195 S |
| 4,107,019 | 8/1978 | Takao et al. | 204/195 S |
| 4,157,282 | 6/1979 | Riddel | 204/195 S |
| 4,177,112 | 12/1979 | Suzuki et al. | 204/1 S |
| 4,177,125 | 12/1979 | Barnabe | 204/195 S |

FOREIGN PATENT DOCUMENTS 2304464 8/1974 Fed. Rep. of Germany ....... 204/195 S
2617031 11/1977 Fed. Rep. of Germany .
2822391 12/1978 Fed. Rep. of Germany .

*Primary Examiner*—T. Tung
*Attorney, Agent, or Firm*—Frishauf, Holtz, Goodman & Woodward

[57] ABSTRACT

To measure partial oxygen pressure in gases, particularly exhaust gases of automotive-type combustion engines, a solid electrolyte plate of elongated rectangular configuration has at least one electrode pair applied to a single surface thereof, which is exposed to the measuring gas. Preferably, the gap between electrodes is elongated, by forming the electrodes in comb-interdigited form. A thermocouple - temperature sensor can be applied between connecting tracks for the electrodes which extend longitudinally of the electrolyte plate towards the other end thereof, through a sealing mass holding the plate within a housing, the other end forming, simultaneously, a connection terminal for connection to an electric connector or plug. A heating element can be placed on the obverse side of the plate, preferably in the position in the gap between the electrodes. More than one such sensor element may be secured in the same housing, and, for example, two such plates, back to back, with the heating element therebetween, spaced from each other, or as a common block. The sensor may be used for potentiometric and/or polarographic measurement, depending upon cover coatings on the electrodes which control exposure thereof to the gases, catalytic or non-catalytic action of the electrodes (for example being of platinum or gold, respectively) and whether a voltage is applied across the electrode terminals, or the sensor is to operate as an electrochemical cell. Such sensor can be inexpensively made, are suitable for mass production, and flexible with respect to their mode of operation.

26 Claims, 9 Drawing Figures

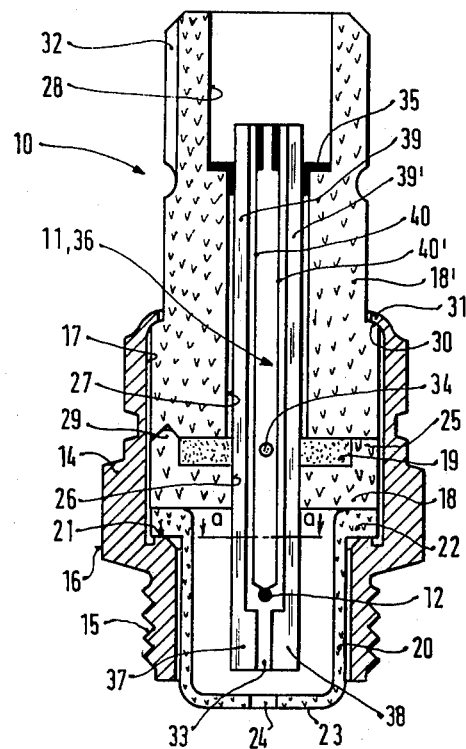
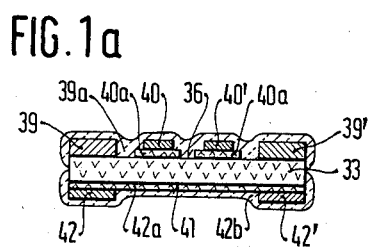
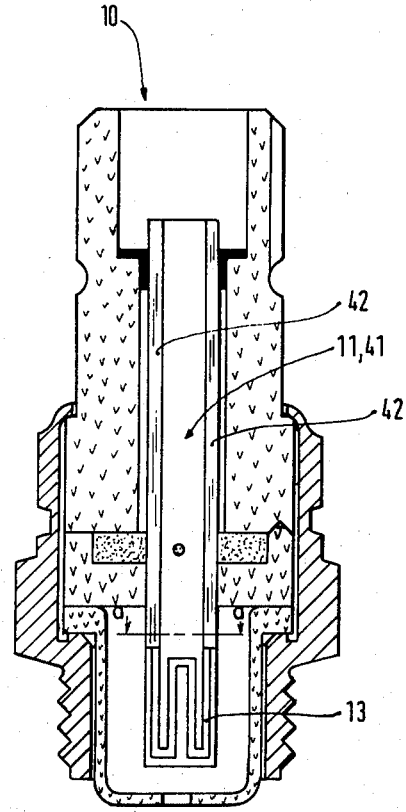

ELECTROCHEMICAL SENSOR STRUCTURE TO DETERMINE OXYGEN CONTENT IN COMBUSTION EXHAUST GASES

Reference to related patents and applications, assigned to the assignee of the present application: U.S. Pat. Nos. 4,157,282, Riddel, 3,691,023, Ruka et al. German Disclosure Document DE-OS 27 11 880 (corresponding to U.S. application Ser. No. 6,093, filed Jan. 24, 1979; CIP of Ser. No. 885,368 of Mar. 13, 1979, abandoned) DIETZ; U.S. Ser. No. 098,602, filed Nov. 29, 1979, FRIESE U.S. Ser. No. 06/098,708, filed Nov. 29, 1979, Hoecker et al (claiming priority of Fed. Rep. Germany Application P 28 52 638.7 of Dec. 6, 1978.

The present invention relates to an electrochemical sensor for the determination of the oxygen content in gases, and more particularly in exhaust gases resulting from combustion processes, and especially for exhaust gases emanating from automotive-type internal combustion engines.

BACKGROUND AND PRIOR ART

Various types of such sensors have been proposed and are described in the general and in the patent literature, and reference is made to the above-referenced patents and applications and publications. The referenced U.S. Pat. No. 4,157,282 describes a plate-like solid electrolyte body on which electrodes are applied at opposite sides, the body being exposed to the gas to be measured, and providing a voltage signals which depends on the oxygen concentration in the test gas. This type of sensor is referred to as a potentiometric sensor. The referenced U.S. Pat. No. 3,691,023 describes a sensor on which a solid electrolyte body is provided in plate form on which electrodes are applied to opposite sides thereof, and on which electrodes a voltage is applied. The electric current to the electrodes will be limited by the gas phase diffusion, and the output signal of the sensor will then depend on the oxygen content of the exhaust gas. This type of sensor, that is, a current limit sensor, is also referred to as a polarographic sensor. The patent also describes a separate heating element for the sensor which provides a suitable working temperature for the solid electrolyte body. U.S. application Ser. No. 6,093, of Jan. 24, 1979, DIETZ, also relates to a polarographic sensor with a porous coating on the sensing electrode, through which the test gas must diffuse. This sensor has a tubular solid electrolyte body with a closed end. The inner space of the tubular body has a reference gas, for example ambient air applied thereto.

The physical construction of such sensors still provides problems, particularly of sensors which are not intended for stationary installation, for example in the smoke stack of a boiler, but rather are to be used in automotive applications where they are subject to widely varying temperature fluctuations, shock and vibration.

The Invention

It is an object to improve electrochemical sensors, and particularly to provide a construction which permits simple and inexpensive manufacture while providing rapid response sensitivity and which is so arranged that it can be combined with a heating element and, if desired, additionally, with a temperature sensor such as thermocouple; and which, preferably, permits use of the sensor, or arrangement thereof, to function both as a potentiometric sensor or as a polarographic sensor, or even to permit the combination of several potentiometric and/or polarographic sensor elements on a single sensor assembly.

Briefly, a metal housing has a sensor element included therein which is an elongated solid electrolyte plate. One pair of electrodes is applied to a single surface of the solid electrolyte plate, and electrically conductive connecting tracks are in electrical contact with the respective electrodes on the single surface and extend the length of the elongated plate and forming, adjacent the end of the plate, connecting terminals. Preferably, the plate is an elongated rectangle. The obverse side of the plate, that is, the side remote from the electrodes, may have a conductive track formed thereon which provides a heating element and, if desired, additionally conductive tracks which extend to a thermocouple so that the plate can be heated to a desired operating temperature.

In accordance with a feature of the invention, a plurality of such plates can be stacked to form a combination assembly, heated, for example, by a single or multiple heating element, sandwiched between two stacked plates, the outsides of which are exposed to the test gas and have the electrodes applied thereto. The electrodes can be in the form of facing electrode surfaces applied to the sensor body, interdigited in the form of comb-like projections, or of other suitable shape. Insulating material can be applied between and/or over the electrodes, particularly porous material to permit penetration of test gas to the electrodes.

DRAWINGS

FIG. 1 is a schematic longitudinal cross-sectional view through a potentiometric sensor, in enlarged representation, and showing the flat side of the sensor plate;

FIG. 1a is a highly schematic cross section of the sensor plate along line a—a of FIGS. 1 and 2, omitting the housing and an outer protective shroud;

FIG. 2 is a longitudinal view through the sensor in accordance with FIG. 1, rotated 180°, and showing the back side of the sensor element;

Figure 7:
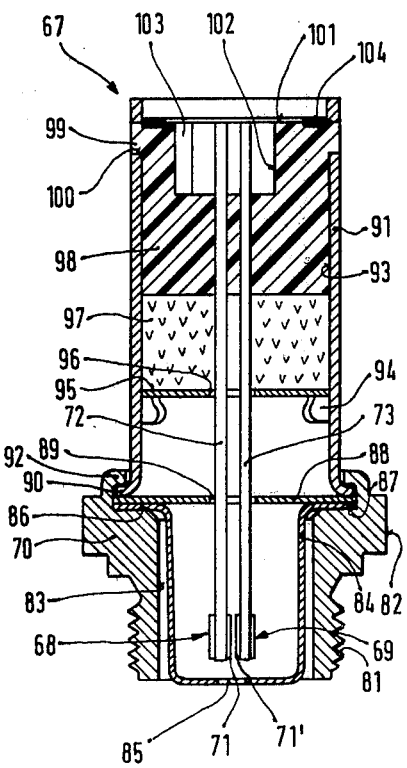
Figure 8:
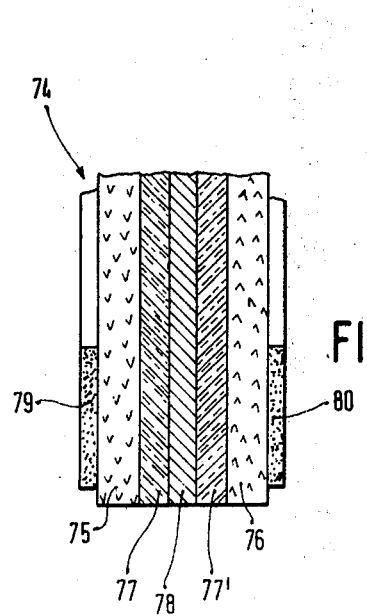

FIG. 7 is a longitudinal cross section through a sensor, to an enlarged scale, having a plurality of potentiometric and/or polarographic sensor elements positioned therein, rotated 90° with respect to the showing of FIGS. 1 or 2; and FIG. 8 is a cross section of the sensing end portion of a sensor element block or assembly, and forming a modification of the sensing portions of the sensor of FIG. 7.

The sensor 10 shown in FIGS. 1 and 2 is used to determine the oxyen content in exhaust gases from internal combustion engines, particularly of the automotive type, and essentially includes a housing 14, typically of steel or other metal suitable for insertion into the exhaust system from an internal combustion engine, within which an elongated rectangular sensing element 11 is retained on which additionally a temperature sensor 12 and a heater element 13 are located. The housing 14 has an outer thread 15 and a hexagonal surface 16 to receive a socket wrench or the like, for installation of the housing in a suitable pipe or tube which carries the exhaust gas. The housing is formed with a longitudinal bore 17 within which holding elements 18, 18' and a seal 19 are provided to secure the sensor element 11 in position within the housing. A protective shield or shroud 20 surrounds the sensor element—with clearance—in the region where the sensor element is exposed to the exhaust gases.

The housing 14 is formed with an internal shoulder 21 within its longitudinal bore 17. The shield 20, which is essentially tubular, has a flange 22 engaging the shoulder 21. The shield 20 may be of any suitable material, for example, and as shown is suitably of ceramic, and has an opening 24 in its bottom 23 to permit ingress of the test gas. The holder or attachment element 18 engages a flange 22 of the shield 20. Element 18 is essentially disk-shaped and has a central opening 26 to permit passage of the sensor element therethrough. Element 18 is formed with an edge 25 which is formed further with a central recess to receive a sealing medium, such as a cement, a glass, or the like, in order to secure the sensor element therein and to seal the sensor element into position and prevent escape of exhaust gases outwardly along the sensor. The edge 25 of the holder element 18 is engaged by an essentially cylindrical ceramic holder element 18' which also defines the upper surface of the sealing substance 19. The holder element 18' is formed with a longitudinal opening 27 to receive the sensor element, and with an upper wider recess 28 into which the end portion of the sensor element remote from the test gas extends. The holders or attachments 18, 18' are located with respect to each other by engagement of a projection 29, formed on the edge 25 of the holder 18 which fits into a matching recess or dimple in the element 18'. The outer side of the element 18' is formed with a shoulder 30 which is engaged by an inwardly peened, rolled or otherwise deformed portion 31 of the metal shell or housing 14. Thus, the protective shield 20, the holder elements 18, 18' and the seal 19 are fixed and secured in the housing 14. Temperature compensating elements which may be inserted in the form of disks, or similar structural units between the holder elements or between any one of the flanges, or which may be used between subdivisions of the respective holder elements, and possibly additional sealing rings, such as O-rings or the like, have been omitted from the drawing for simplicity; such temperature compensation arrangements are well known. The outer side of the holder 18' additionally has a locating groove 32 formed therein to provide a locating index for an overlapping portion of a connecting cable which can be inserted into the enlarged recess 28.

The sensor element 11 consists of an oxygen ion conductive solid electrolyte plate 33, essentially consisting of stabilized zirconium dioxide, and having a dimension of about 8 mm width and a thickness of about 0.8 mm, that is, a thickness to width ratio of about 1:10. The stabilized zirconium dioxide solid electrolyte plate 33 extends with one end portion into the region of the sensor 10 which has test gas applied thereto, surrounded by the protective shield 20. The plate 33 then extends through the fitted opening 26 in the holder 18, through the positioning and sealing mass 19, through the fitted longitudinal opening 27 in the holder element 18', and terminates with the other end portion in the enlarged recess 28 of the holder 18'. The sensor, effectively has a sensing end portion, a holding or terminal end portion, and an intermediate sealing and locating portion. The sensor element 11 is longitudinally fixed in position by a cross bore 34, formed in the region of the seal 19, which will penetrate through the cross bore before setting or hardening or solidifying, depending on the material for the seal 19, and which fixes the plate in position. The plate is additionally secured in the solid electrolyte body 33 by an upper holding element 35 which extends from the enlarged recess 28 alongside the plate 11 and into the longitudinal opening 27. Preferably, the upper attachment of sealing and holding element is silicone rubber. Other plastic materials may be used.

The front side 36 of the solid electrolyte plate 33 has two electrodes 37, 38 (FIG. 1) applied thereto, so that the electrodes will be positioned in a region washed by the test gas. The electrodes 37, 38 are flat, that is, in plate form, and can be applied by any known suitable process, for example by printing, spraying, or vapor deposition. Screen printing is a suitable process. The electrodes 37, 38 are connected to conductive strips 39, 39', likewise applied to the solid electrolyte plate. The conductive strips or tracks are so placed that the track 39 extends at the left front edge and the track 39' at the right longitudinal edge of the front side 36 of the solid electrolyte plate 33. Both conductive tracks 39, 39' are carried through to the end portion of the plate 33 which extends into the recess 28, where they will form electrical connecting terminals. The electrode 37, for example of platinum, and the electrode 38, for example of a catalytically less active material than the electrode 37, for instance gold, and preferably also the portions of the conductive tracks 39, 39' which are within the region washed by the test gas, are all covered with a porous protective layer 39a (FIG. 1a) which, for example, may consist essentially of magnesium spinel. Methods to apply such coatings to the electrode are well known. The front side 36 of the solid electrolyte plate 33 additionally has a thermo element 12 applied thereto in accordance with any known and suitable method. The thermo element or thermocouple 12 is positioned between the tracks 39, 39', and preferably located close to the electrode pair 37, 38. The temperature sensor 12 is connected to two connecting tracks 40, 40' which extend to the terminal end of the plate 33 which is positioned within the enlarged recess 28. The tracks 40, 40' are separated from the solid electrolyte plate 33 by means of an insulation layer 40a, for example of aluminum oxide, and applied by plasma spraying on the solid electrolyte plate 33 (see FIG. 1a). Alternatively—although functionally less effective—it is possible to apply the temperature sensor to the back side 41 of the solid electrolyte plate 33.

The back side 41 (FIG. 2) of the solid electrolyte plate 33 has a heater element 13 positioned in the region washed by the test gas. The heater element 13 may, of example, be applied as a conductive strip of platinum, and secured to the plate by any well known process, such as printing, spraying, or vapor deposition. It is separated from contact with the solid electrolyte plate by an insulation layer 42a, for example also of aluminum oxide. The aluminum oxide layer may be applied to the solid electrolyte plate, 33 for example by plasma spraying. The heater element portion, as well as the connecting tracks or strips 42, 42', are thus applied—with interposition of the insulating layer—on the solid electrolyte plate, and supported thereby. To suppress undesired reaction between the heater element 13 and the test gas, the heater element 13 is covered with a thick coating 42b, essentially non-porous to the test gas. This coating may consist, for example, of glass. The heater element 13 need not be located at the back side 41 of the plate 33; it could be positioned at the front side 36, particularly if the thermocouple 12 is relocated to the back side 41; the arrangement may also be so modified that both the front side 36 as well as the back side 41 each have a heater element 13 applied thereto.

The arrangement of the electrodes on the end portion of the solid electrolyte body which is exposed to the test gas can be selected in various configurations. Thus, FIG. 1 shows two elongated electrodes 37, 38, facing each other with a gap therebetween.

Figure 3:
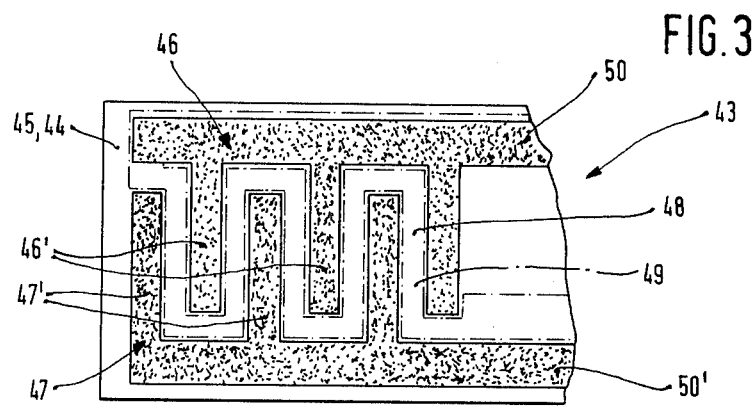
FIG. 3 is a greatly enlarged schematic view of the terminal portion of the sensor element illustrating the electrode side, having interdigited comb electrodes and, schematically, also showing a particularly suitable heating element arrangement.

Embodiment of FIG. 3: The sensor element 43 has a solid electrolyte body 44 which, on its front side 45, has comb electrodes 46, 47 positioned so that the comb projections are interdigited. The comb electrodes 46, 47 have their projections 46', 47' fitted within each other, with a gap 48 therebetween—see FIG. 3. The back side of the solid electrolyte body 44 has the insulating layer 42a (FIG. 1a) applied thereto, on which a heating element 49—in flat layer form—is so arranged that it is positioned in that region in which the gap 48 occurs at the front side of the solid electrolyte body 44. The path of the heater strip on the side obverse to the front side 45 is shown in chain-dotted lines in FIG. 3. This arrangement provides for heating especially of that region of the solid electrolyte plate in which the oxygen ion conduction takes place.

The projections or tines 46', 47' of the comb electrodes can also be so arranged that the ends of the tines connected with the conductive strips 50, 50' are wider, or are dimensioned to be thicker than the free ends of the tines 46', 47', respectively. Making the tines wider or thicker at the ends adjacent the conductive tracks 50, 51 equalizes, at least approximately, the current density through the respective sections of the electrodes 46, 47.

The right and left sides—with respect to FIG. 3—of the tines 46',47' need not be straight but can be zig-zag formed, that is, have their own small projecting triangular or square teeth so as to have crenelated appearance, preferably also interdigited with respect to similar projections on the opposite tine. Interdigited arrangements, and composite interdigited arrangements, that is, with further projections and valleys therebetween on the lateral surfaces of the tines themselves, increases the electrode activity of the sensor element 43.

The sensor element 43 can be installed and assembled into the housing 14 in the same manner as described in connection with FIGS. 1 and 2.

The sensor 10, with the sensor elements 11 or 43, respectively (FIGS. 1, 2; FIG. 3) operates in the form of an oxygen ion concentration sensor with an ion conductive solid electrolyte body and provides a voltage signal which depends on the partial oxygen pressure of the test gas, that is, similar to the sensor described in the referenced U.S. Pat. No. 4,157,282.

Figure 4:
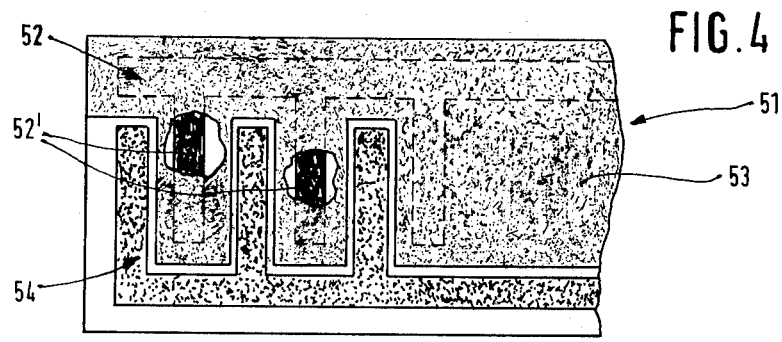
FIG. 4 is a greatly enlarged flat view of a polarographic sensor element with interdigited electrodes and, additionally, showing arrangement of a heater element therefor.

Embodiment of FIG. 4: The sensor element 51 can be assembled in a sensor 10 similar to that shown in FIGS. 1 and 2. The end portion of the sensor element 51 exposed to the test gas differs from the sensor element 43 in construction only in that the porous cover layer covering one of the electrodes, for example the electrode 42 with its tines or projections 52', forms a diffusion barrier 53 for oxygen molecules in the test gas. This electrode preferably consists of platinum or a platinum-based or platinum-type metal. The porous cover layer 53, like the porous cover layer 39a (FIG. 1) may consist of magnesium spinel. Depending on the desired operation, that is, of the type of sensor, the porosity and/or the thickness of the cover layer will be different however. The diffusion barrier 53 may also cover the electrode 54 and will then there act as a porous coating. The electrode 52, and possibly the counter electrode 54, which likewise may be of platinum, of the sensor 51 has a voltage of about 1 V applied thereacross. The level of the current limited by gas diffusion provides an output signal or a value which depends on oxygen partial pressure. Sensor elements 51 which so operate are, by themselves, known and referred to as polarographic sensors and described, for example, in the referenced U.S. Pat. No. 3,619,023, and application 6,093, Jan. 24, 1979, DIETZ, and its published equivalent, German Disclosure Document DE-OS 27 11 880, assigned to the assignee of this application.

Figure 5:
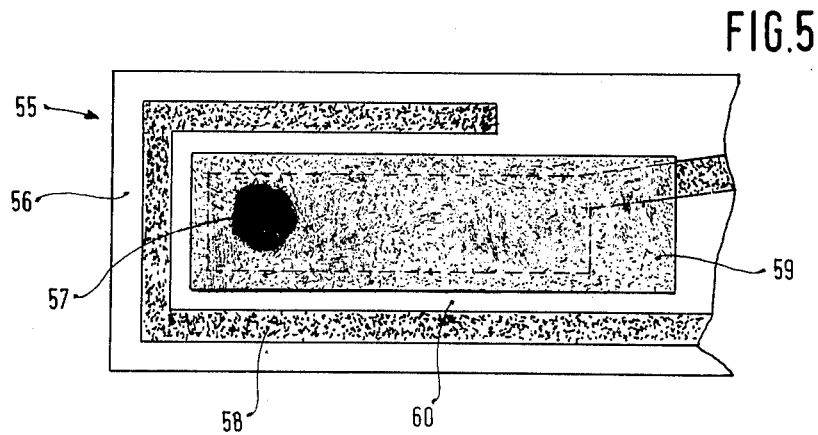
FIG. 5 is an enlarged end view of a polarographic sensor illustrating yet another arrangement of electrodes.

Embodiment of FIG. 5: The end portion of the sensor element 55 exposed to the test gas is shown to greatly enlarged scale, in which a solid electrolyte plate 56 has electrodes 57, 58 applied thereto. The configuration of electrodes 57, 58 differs from that of the electrodes 52, 54 of FIG. 4. The electrode 57 which, in case of a polarographic sensor, is covered with a diffusion barrier 59, is shaped in form of a plate; the other electrode, 58, is hook-like and surrounds the plate, or an essentially rectangular electrode 57, see FIG. 5. A gap 60 separates the two electrodes. The hook-like electrode 58 may, likewise, be covered with a porous protective layer, which has been omitted from FIG. 5 for clarity.

If the sensor element 55 is to operate as a potentiometric sensor, then its electrode construction may remain, but the thickness and/or the porosity of the cover layer, as well as the electrode materials must be matched to the changed requirements.

The heating element which, preferably, is located on the back side or obverse side of the electrode plate 56 is preferably positioned in that region in which, on the front side 56, the gap 60 between the electrodes 57, 58 is located.

Suitable dimensions and/or characteristics of the respective cover coatings over the electrodes are known, and described in the referenced patents.

Figure 6:
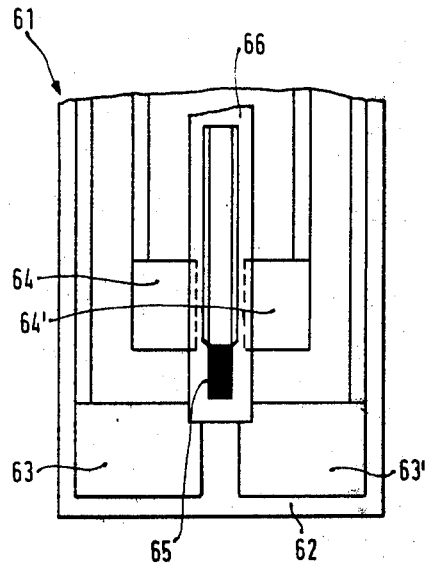
FIG. 6 is a schematic front view of the sensing end portion of a sensor element having two electrode pairs.

Embodiment of FIG. 6: A sensor element 61 has a solid electrolyte plate 62 on which two electrode pairs 63/63' and 64/64' are secured. Each one of the electrode pairs have their own individual connecting tracks extending towards the outer end portion of the solid electrolyte plate, for connection to external conductors. A temperature sensor 65 is located centrally between the electrode plates, connected to its own connecting tracks for further connection to an outside circuit. The electrode pairs 63/63' and 64/64' suitably are applied to a single side of the solid electrolyte plate 62. The distance of the electrode pairs 63/63' from the electrode pairs 64/64' is so selected that the electrode pairs do no functionally influence each other. The electrode pairs will be covered with protective and diffusion layers, as previously described. The protective and diffusion layers for the respective electrode pairs 63/63' and 64/64' need not be the same; thus, one electrode pair may have a protective layer applied thereto which results in operation of the sensor portion between those electrodes for potentiometric measurement; the other electrode pair will have a protective layer applied thereto which functions as a diffusion barrier for one of the electrodes so that the other electrode pair can be used for polarographic measurement. Of course, both electrode pairs may have the respective layers similarly applied so that both electrode pairs function either as potentiometric sensors or as polarographic sensors.

The temperature sensor 65, preferably a thermo element or thermocouple, is insulated from the electrode pairs 63/63' and 64/64' by means of insulating layer 66. The obverse side of the solid electrolyte plate 62 may, and preferably has, as in the other examples, a heating element applied thereto.

A plurality of sensors may be secured in a single metallic housing. One such embodiment is illustrated in FIG. 7: Sensor 67 has a metallic housing 70 in which two sensor elements 68, 69 are located. The sensor elements 68, 69, secured in the single housing 70, are sensor elements as described in the foregoing examples. Preferably, they are arranged in pairs and parallel to each other, with some distance from each other. If needed, each one may have its own heating element 71, 71' applied thereto, preferably at the sides facing each other, in order to obtain efficient utilization of heating energy. In most instances it may suffice if only one of the two sensor elements, that is, either element 68 or 69, have a single heating element, that is, either heating element 71 or 71', respectively, supplied thereto; this is particularly appropriate if the sensor elements 68, 69 are positioned close to each other or, possibly, are in direct engagement with each other. The respective heating element 71 or 71' is insulated from the solid electrolyte body 72 and 73, for example by an insulation layer of aluminum oxide, similar to layer 42a-FIG. 1a- and/or by an air gap.

FIG. 8 illustrates the sensing end portion of a sensor element block 78, carrying a multiplicity of sensing elements. The sensing element block 74 has two electrolyte plates 75, 76 which face each other with their back sides, separated by an insulation layer 77, 77' (e.g. glass, aluminum oxide), and between which a common heating element 78 is positioned. At the outer respective surfaces, the solid electrolyte plates 75, 76 each support a pair of electrodes 79, 80; more than one pair of electrodes may be positioned at the outer surfaces—see FIG. 6. A temperature sensor, not shown in FIG. 8, may likewise be applied—see FIGS. 1 and 6. The temperature sensor and the respective electrodes are insulated from each other and/or the solid electrolyte plate 75, respectively. The sensor element block 74 forms a securely connected and joined unit and can be used simultaneously or temporally staggered, for potentiometric and/or polarographic measurements.

Sensor 67 which has the two sensor elements 68, 69 (FIG. 7), or one or more sensor element blocks 74 (FIG. 8), is positioned in a metallic housing 70 with an outer thread 80 and a socket-engagement surface 82 for assembly into a tube or pipe through which the test gas flows. The portion of the sensor elements 68, 69 exposed or washed by the test gas extends into the longitudinal bore 83 of the housing 7 and is positioned—with clearance—within a metallic shield or shroud or protective cap 84 having an opening 85 in its bottom for the test gas. The other end portion of the shield 84 is formed with a flange 86 which is engaged on a shoulder 87 formed in the longitudinal opening 83 of the housing structure 70. The shoulder 87 additionally supports a metallic reflection shield 88, formed with a central bore or opening 89 through which the sensor elements 68, 69 or 74, respectively, extend. The reflector disk or shield 88 has a heat reflecting coating or surface facing downwardly—FIG. 7—in order to localize heat in the region where the sensing element and the electrodes are positioned. Such a heat shield or heat disk is of advantage for localization of high-temperature regions, and particularly advantageous if the inner side of the protective cap or shield 84, as well as the side of the reflection shield or disk 88, all have a heat reflecting surface thereon. A carrier sleeve 91 is engaged on the flange 90 of the reflection shield, extending coaxially with respect to the longitudinal opening 83 of the housing. The carrier flange 90, the reflection shield 88, and the protective cap or shield 84 are all secured to the shoulder 87 of the housing by an overlap flange 92 extending from the housing 70. Above the flange 90, the sleeve 91 has inwardly extending punches or noses 94 in order to support a metal disk 95, formed with a central bore 96 through which the sensor elements 68, 69 or block 74, respectively, extend, the punches or noses forming support elements for a plurality of retaining disks 97, shown only as a single element. The retaining disks 97 which, for example, are of ceramic, retain the heat within the lower portion of the sensor element and protect the upper portion therefrom by separating heat from the sensor element holder 98 which is positioned in the upper portion of the sleeve 91 and which, for example, may consist of a plastic, for example a fiberglass reinforced thermosetting resin. Rather than using plastic, the sensor holding structure 98 itself may consist of glass or of suitable ceramic. Preferably, the sensor element holder 98 is applied by injection molding into the sleeve 91 which, simultaneously, fixes the sensor elements 68, 69, or 74, the reflection shield 88, and the heat blocking layers 97 in position. The injection molding process also applies locating projections 99 which fit into corresponding openings 100 in the walls of the carrier sleeve 91 to secure the material 98 in position therein and enter it reliably in place. The end portion of the sensor holder element 98 preferably has its facing end surface 101 recessed with a recess or bore 102, which can be formed in the same step during the injection molding operation, and into which the end portions of the sensor elements 68, 69, or 74, respectively, extend. The recess has a locating and holding groove 103 for a standard connecting plug which can be inserted in the recess 102 to make connections with the respective current paths or tracks extending along the facing surfaces of the central element or element combination or assembly. A sealing ring 104 is located at the outer periphery of the holding element 98 in order to provide for a tight connection of a plug with the sensor unit as a whole and the sensing elements themselves.

Various changes and modifications may be made, and features described in connection with any one of the embodiments may be used with any of the others, within the scope of the inventive concept.

We claim:

1. Electrochemical sensor to determine the oxygen content in gases, more particularly of combustion exhaust gases, and especially for exhaust gases from automotive-type engines, comprising, the structural arrangement of a metal housing (14, 70);

a sensor element (11, 43, 51, 55, 61, 68, 69, 74) which includes an elongated solid electrolyte plate (33, 44, 56, 62, 72, 73, 75, 76) longitudinally positioned in the housing, the sensor element having a holding end portion located and secured in the housing and a sensing end portion exposed to the exhaust gases and at least one electrode pair (37, 38; 46, 47; 52, 54; 57, 58; 63, 63'; 64, 64'; 68, 69, 79, 80) located and secured on a single surface (36, 45) of the solid electrolyte plate, adjacent said sensing end portion exposed to the gas;

the electrodes (46, 47; 52, 54; 57, 58) of the pairs facing each other across a gap (48, 60);

the facing edges of the electrodes being formed with extending projections extending towards the other electrode in interdigited relationship;

and electrically conductive connecting tracks (39, 39'; 50, 50') in electrical contact with respective electrodes of at least one electrode pair secured to and applied on said single surface of the solid electrolyte plate, and extending essentially for the length thereof from the electrodes to the holding end portion and forming, adjacent the end of the plate, connecting terminals.

2. Sensor according to claim 1, wherein the extending projecting portions project towards each other in interdigited, comb form.

3. Sensor according to claim 1, further including a temperature sensing element (12, 65) located on the sensor element;

and an insulating layer (40a, 66) separating the temperature sensing element from said solid electrolyte plate, said electrodes and said connecting tracks.

4. Sensor according to claim 3, wherein the temperature sensing element comprises a thermo element located close to and in heat transfer and sensing relationship with respect to the portion of the solid electrolyte body which is immediately beneath the electrodes.

5. Sensor according to claim 1, further including a planar heating element (13, 49, 71, 71', 78) located on the solid electrolyte plate;

and a layer of insulating material (42a, 66) separating the planar heating element from the solid electrolyte plate.

6. Sensor according to claim 5, wherein the heating element (13, 49, 71, 71', 78) is on the side opposite said single side of the solid electrolyte plate (33, 44, 62, 72, 73, 75, 76).

7. Sensor according to claim 6, wherein the heating element (49) on the solid electrolyte plate is positioned thereon on said opposite side in the region of the gap between the electrodes of the pair.

8. Sensor according to claim 5, further including conductive tracks located on the insulating layer applied to the surface of the solid electrolyte plate on which the planar heating element is positioned connecting to the heating element and extending lengthwise of the plate towards the holding end portion.

9. Sensor according to claim 4, further including connecting tracks located on an insulating layer secured to the surface on which the temperature sensor is positioned, and in electrical contact with the temperature sensor and extending to the holding end portion of the plate and forming connection terminals for a sensing connection thereto.

10. Sensor according to claim 1, wherein one of the electrodes (37, 46) of the electrode pair applied to said one single side of the sensor element (11, 43) is catalytically active, and the second electrode (38, 47) is catalytically less active than said first electrode;

and wherein the connecting tracks (39, 39'; 50, 50') provide output signals from the sensor, said sensor functioning as an electrochemical cell.

11. Sensor according to claim 1, further including a diffusion barrier (53, 59) applied to at least one of the electrodes of the electrode pair (52, 54; 57, 58), said diffusion barrier providing a diffusion impediment to oxygen molecules within the gases;

said sensor, upon having a voltage applied to the electrodes via the conductive tracks connected thereto, operating as a polarographic sensor.

12. Sensor according to claim 11, wherein the diffusion barrier (53, 59) is a porous layer.

13. Sensor according to claim 10, further including a protective cover layer (39a) which is porous in the region of the electrodes and covering the electrodes and at least adjacent portions of the connecting tracks.

14. Sensor according to claim 13, further including a temperature sensor and temperature signal connecting tracks applied to a surface of said solid electrolyte plate;

a planar heating element (13) and connecting tracks applied to a surface of said solid electrolyte plate;

and wherein the protective cover layer also covers the temperature sensing element at least portions of the temperature sensing connecting tracks, the heating element, and at least adjacent portions of the heating connecting tracks.

15. Sensor according to claim 11, further including a protective cover layer covering the electrode free from the diffusion barrier and at least adjacent portions of the connecting tracks.

16. Sensor according to claim 15, further including a temperature sensing element and temperature signal connecting tracks applied to a surface of said solid electrolyte plate;

a planar heating element (13) and connecting tracks applied to a surface of said solid electrolyte plate;

and wherein the protective cover layer also covers the temperature sensing element at least portions of the temperature sensing connecting tracks, the heating element, and at least adjacent portions of the heating connecting tracks.

17. Sensor according to claim 1, wherein the housing (14, 70) is an essentially tubular element with a central opening or bore;

and separating and sealing means (19, 97, 98) separating the essentially tubular element into a sensing region adapted to be exposed to the exhaust gases, and a holding and connecting region adapted to be remote from the exhaust gases, the separating and sealing means seating and retaining the sensing elements in an intermediate portion;

the sensing portion carrying the electrodes being located in said sensing region and the holding portion being located in the connecting region.

18. Sensor according to claim 17, further including heat reflecting heat shield means (88) forming part of said separating and sealing means, and having a heat reflecting surface directed towards the sensing region.

19. Sensor according to claim 17, wherein a pair of sensor elements (68, 69; 75, 76) are positioned in the metal housing, with said single surfaces on which the electrodes are applied facing away from each other;

and further including at least one heating element (71, 71', 78) located adjacent the facing surfaces of said sensor elements.

20. Sensor according to claim 19, wherein the sensor elements are spaced from each other, and each sensor element has an individual heating element applied at the surface facing the other sensor element.

21. Sensor according to claim 19, wherein the sensor elements are stacked one on the other, and a single heating element (78) is located between the sensor elements (75/79, 76/80) to form a composite sensing block.

22. Sensor according to claim 1, further including a protective cap (20, 84) extending from the housing and surrounding the portion of the sensor element exposed to the exhaust gases, said cap being formed with an opening (24, 85) therein to permit ingress of a measured quantity of said exhaust gases to said sensor elements and the electrodes thereon.

23. Sensor according to claim 18, further including a protective cap (20, 84) extending from the housing and surrounding the portion of the sensor element exposed to the exhaust gases, said cap being formed with an opening (24, 85) therein to permit ingress of a measured quantity of said exhaust gases to said sensing elements and the electrodes thereon to form, together with said heat reflective heat shield means a thermo chamber for collection of said gases to wash over the sensor element.

24. Sensor according to claim 1 wherein the approximate ratio of thickness to width of the plate is 1 to 10.

25. Sensor according to claim 1 wherein the elongated plate comprises stabilized zirconium dioxide of a thickness of about 0.8 mm, and of a width of about 8 mm.

26. Electrochemical sensor to determine the oxygen content in gases, more particularly of combustion exhaust gases, and especially for exhaust gases from automotive-type engines, comprising, the structural arrangment of:

A metal housing (14,70);

A sensor element (11, 43, 51, 55, 61, 68, 69, 74) which includes an elongated solid electrolyte plate (33, 44, 56, 62, 72, 73, 75, 76) longitudinally positioned in the housing, the sensor element having a holding end portion located and secured in the housing and a sensing end portion exposed to the exhaust gases, and at least one electrode pair (37, 38; 46, 47; 52, 54; 57, 58; 63, 63'; 64, 64'; 68, 69, 79, 80) located and secured on a single surface of the solid electrolyte plate adjacent said sensing end portion exposed to the gas;

the electrodes (46, 47; 52, 54; 57, 58) of the pairs facing each other across a gap (48, 60);

one of the electrodes has a central portion located essentially centrally on said single side of the electrolyte plate and the other electrode has a hook-like portion looping in part around the central portion of said one electrode;

and electrically conductive connecting tracks (39, 39'; 50, 50') in electrical contact with respective electrodes of at least one electrode pair secured to and applied on said single surface of the solid electrolyte plate, and extending essentially for the length thereof from the electrodes to the holding end portion and forming, adjacent the end of the plate, connecting terminals.

* * * * *